United States Patent
Dunican et al.

(10) Patent No.: US 7,901,913 B2
(45) Date of Patent: Mar. 8, 2011

(54) PROCESS FOR THE PREPARATION OF L-AMINO ACIDS BY OVEREXPRESSING THE TAL GENE ENCODING TRANSALDOLASE

(75) Inventors: Laurence Kieran Dunican, Galway (IE); Rita Dunican, legal representative, Galway (IE); Ashling McCormack, Athlone (IE); Cliona Stapelton, Roscrea (IE); Kevin Burke, Galway (IE); Bettina Mockel, Bielefeld (DE)

(73) Assignee: Evonik Degussa GmbH, Essen (DE)

( * ) Notice: Subject to any disclaimer, the term of this patent is extended or adjusted under 35 U.S.C. 154(b) by 547 days.

(21) Appl. No.: 10/847,610

(22) Filed: May 18, 2004

(65) Prior Publication Data
US 2004/0214219 A1 Oct. 28, 2004

Related U.S. Application Data

(62) Division of application No. 09/531,266, filed on Mar. 20, 2000, now Pat. No. 6,797,509.

(60) Provisional application No. 60/142,915, filed on Jul. 9, 1999.

(51) Int. Cl.
*C12P 13/04* (2006.01)
*C12N 15/74* (2006.01)
*C12N 9/98* (2006.01)

(52) U.S. Cl. .......................... 435/106; 435/471; 435/187

(58) Field of Classification Search .................. None
See application file for complete search history.

(56) References Cited

U.S. PATENT DOCUMENTS

2004/0180408 A1* 9/2004 Pompejus et al. ........... 435/69.1

FOREIGN PATENT DOCUMENTS

| EP | 0699759 A1 | 3/1996 |
|---|---|---|
| EP | 0629699 B1 | 12/1998 |
| EP | 1 108 790 | 6/2001 |
| JP | 3-147791 | 6/1991 |
| JP | 03-147792 | 6/1991 |
| JP | 09 224661 | 9/1997 |
| WO | WO 01/00844 | 1/2001 |

OTHER PUBLICATIONS

Pompejus et al. (1999) US provisional application filed on Jul. 9, 1999.*
Labarre et al. (1993) Journal of Bacteriology, vol. 175, p. 1001-1007.*
Guo et al., Protein tolerance to random amino acid change, (2004) Proc. Natl. Acad. Sci. USA 101: 9205-9210.*
Lazar et al., Trnasforming Growth Factor alpha: Mutation of aspartic Acid 47 and Leucine 48 Results in Different Biological Activities, (1988) Mol. Cell. Biol. 8:1247-1252.*
Hill et al., Functional Analysis of Conserved Histidines in ADP-Glucose Pyrophosphorylase from *Escherichia coli*, (1998) Biochem. Biophys. Res. Comm. 244:573-577.*
Koffas et al., Sequence of the *Corynebacterium glutamicum* pyruvae carboxylase gene., Appl Microbiol Biotechnol, 1998, vol. 50, pp. 346-352.*

(Continued)

*Primary Examiner* — Alexander D Kim (57) ABSTRACT

The invention is directed to DNA sequences from coryneform bacteria, particularly *Corynebacterium glutamicum*, which encode a protein having transaldolase enzymatic activity. The invention also encompasses processes for the fermentative production of L-amino acids using bacteria in which a gene encoding transaldolase is amplified.

16 Claims, 1 Drawing Sheet

OTHER PUBLICATIONS

Uwe Kohler et al., "Transaldolase genes from the cynobacteria *Anabaena variabilis* and *Synechocystis* sp. PCC 6803: comparison with other eubacterial and eukaryotic homologues," Plant Molecular Biology, vol. 30, 1996, p. 213-218.

Colón, et al., "Production of Isoleucine by Overexpression of ilvA in a *Corynebacterium lactofermentum* Threonine Producer," *Appl. Microbiol. Biotechnol.*, 1995, 43(3):482-488 (abstract only).

Cremer, et al., "Control of the Lysine Biosynthesis Sequence in *Corynebacterium glutamicum* as Analyzed by Overexpression of the Individual Corresponding Genes," *Appl. Environ. Microbiol.*, 1991, 57(6):1746-1752.

Jia, et at., "Crystal Structure of Transaldolase B from *Escherichia coli* Suggests a Circular Permutation of the Alpha/Beta-Barrel within the Class I Aldolase Family," *Structure*, 1996, 4(6):715-724 (abstract only).

Hung, et al., "In Vivo Selected Promoter and Ribosome Binding Site Upmutations: Demonstration that the *Escherichia coli* bla Promoter and a Shine-Dalgarno Region with Low Complementarity to the 16S Ribosomal RNA Function in *Bacillus subtilis,*" *Mol. Gen. Genet.*, 1989, 219(1-2):129-136 (abstract only).

Reinscheld, et al., "Analysis of a *Corynebacterium glutamicum* hom Gene Coding for a Feedback-Resistant Homoserine Dehydrogenase," *J. Bacteriol.*, 1991, 173(10):3228-3220.

Yanofsky, et al., "Some Novel Transcription Attenuation Mechanisms Used by Bacteria," *Biochimie*, 1996, 78(11-12):1017-1024 (abstract only).

Jia et al., "Crystal structure of the reduced Schiff-base intermediate complex of transaldolase B from *Escherichia coli*: Mechanistic implications for class I aldolases," Protein Science, 1997, 6:119-124.

Köhler et al., "Transaldolase genes from the cyanobacteria *Anabaena variabilis* and *Synechocystis* sp. PCC 6803: comparison with other eubacterial and eukaryotic homologues," Plant Molecular Biology, 1996, 30:213-218.

Lindqvist et al., "Circular permutations of natural protein sequences: structural evidence," Current Opinion in Structural Biology, 1997, 7:422-427.

Morinaga et al., "Expression of *Escherichia coli* promoters in *Brevibacterium lactofermen* turn using the shuttle vector pEB003," Journal of Biotechnology, 1987, 5:305-312.

Jia et al., "Crystal structure of transaldolase B from *Escherichia coli* suggests a circular permutation of the $\alpha/\beta$ barrel within the class I aldolase family," Structure, 1996, vol. 4, No. 6, pp. 715-724.

Karft et al., "Transcription analysis and nucleotide sequence of tox promoter/operator mutants of corynebacteriophage $\beta$," Microbial Pathogenesis, 1992, vol. 13, pp. 85-92.

Patek et al., "Promoters from *Corynebacterium glutamicum*: cloning, molecular analysis and search for a consensus motif," Microbiology, 1996 vol. 142, pp. 1297-1309.

Schörken et al., "Disruption of *Escherichia coli* transaldolase into catalytically active monomers: Evidence against half-of-the-sites mechanism," FEBS Letters, 1998, vol. 441, pp. 247-250.

Sprenger et al., "Transaldolase B of *Escherichia coli* K-12: Cloning of Its Gene, talB, and Characterization of the Enzyme form Recombinant Strains," Journal of Bacteriology, 1995, vol. 177, No. 20, pp. 5930-5936.

* cited by examiner

Figure 1:

SEQUENCE LISTING

```
<160> NUMBER OF SEQ ID NOS: 6

<210> SEQ ID NO 1
<211> LENGTH: 6995
<212> TYPE: DNA
<213> ORGANISM: Corynebacterium glutamicum
<220> FEATURE:
<221> NAME/KEY: CDS
<222> LOCATION: (2471)..(3550)
<223> OTHER INFORMATION: tal-Gen

<400> SEQUENCE: 1
cacatttgaa ccacagttgg ttataaaatg ggttcaacat cactatggtt agaggtgttg      60
acgggtcaga ttaagcaaag actactttcg gggtagatca cctttgccaa atttgaacca     120
attaacctaa gtcgtagatc tgatcatcgg atctaacgaa aacgaaccaa aactttggtc     180
ccggtttaac ccaggaagga ttgaccacct tgacgctgtc acctgaactt caggcgctca     240
ctgtacgcaa ttacccctct gattggtccg atgtggacac caaggctgta gacactgttc     300
gtgtcctcgc tgcagacgct gtagaaaact gtggctccgg ccacccaggc accgcaatga     360
gcctggctcc ccttgcatac accttgtacc agcgggttat gaacgtagat ccacaggaca     420
```

```
ccaactgggc aggccgtgac cgcttcgttc tttcttgtgg ccactcctct ttgacccagt      480
acatccagct ttacttgggt ggattcggcc ttgagatgga tgacctgaag gctctgcgca      540
cctgggattc cttgacccca ggacaccctg agtaccgcca caccaagggc gttgagatca      600
ccactggccc tcttggccag ggtcttgcat ctgcagttgg tatggccatg gctgctcgtc      660
gtgagcgtgg cctattcgac ccaaccgctg ctgagggcga tccccattc gaccaccaca       720 tctacgtcat tgcttctgat ggtgacctgc aggaaggtgt cacctctgag gcatcctcca      780
tcgctggcac ccagcagctg gcaaccctca tcgtgttctg ggatgacaac cgcatctcca      840
tcgaagacaa cactgagatc gctttcaacg gacgttgt tgctcgttac aaggcttacg        900
gctggcagac cattgaggtt gaggctggcg aggacgttgc agcaatcgaa gctgcagtgg      960
ctgaggctaa gaaggacacc aagcgaccta ccttcatccg cgttcgcacc atcatcggct     1020
tcccagctcc aactatgatg aacaccggtg ctgtgcacgg tgctgctctt ggcgcagctg     1080
aggttgcagc aaccaagact gagcttggat tcgatcctga gctcacttc gcgatcgacg      1140 atgaggttat cgctcacacc cgctccctcg cagagcgcgc tgcacagaag aaggctgcat     1200
ggcaggtcaa gttcgatgag tgggcagctg ccaaccctga gaacaaggct ctgttcgatc     1260
gcctgaactc ccgtgagctt ccagcgggct acgctgacga gctcccaaca tgggatgcag     1320
atgagaaggg cgtcgcaact cgtaaggctt ccgaggctgc acttcaggca ctgggcaaga     1380
cccttcctga gctgtggggc ggttccgctg acctcgcagg ttccaacaac accgtgatca     1440
agggctcccc ttccttcggc cctgagtcca tctccaccga gacctggtct gctgagcctt     1500
acggccgtaa cctgcacttc ggtatccgtg agcacgctat gggatccatc ctcaacggca     1560
tttccctcca cggtggcacc cgcccatacg gcggaaccttt cctcatcttc tccgactaca    1620
tgcgtcctgc agttcgtctt gcagctcctca tggagaccga cgcttactac gtctggaccc     1680
acgactccat cggtctgggc gaagatggcc aacccacca gcctgttgaa accttggctg      1740
cactgcgcgc catcccaggt ctgtccgtcc tgcgtcctgc agatgcgaac gagaccgccc     1800
aggcttgggc tgcagcactt gagtacaagg aaggccctaa gggtcttgca ctgacccgcc     1860
agaacgttcc tgttctggaa ggcaccaagg agaaggctgc tgaaggcgtt cgccgcggtg     1920
gctacgtcct ggttgagggt tccaaggaaa ccccagatgt gatcctcatg ggctccggct     1980
ccgaggttca gcttgcagtt aacgctgcga aggctctgga agctgagggc gttgcagctc     2040
gcgttgtttc cgttccttgc atggattggt tccaggagca ggacgcagag tacatcgagt     2100
ccgttctgcc tgcagctgtg accgctcgtg tgtctgttga agctggcatc gcaatgcctt     2160
ggtaccgctt cttgggcacc cagggccgtg ctgtctccct tgagcacttc ggtgcttctg     2220
cggattacca gaccctgttt gagaagttcg gcatcaccac cgatgcagtc gtggcagcgg     2280
ccaaggactc cattaacggt taattgccct gctgttttta gcttcaaccc ggggcaatat     2340
gattctccgg aattttattg ccccgggttg ttgttgttaa tcggtacaaa gggtcttaag     2400
cacatccctt acttgcctgc tctccttgag cacagttcaa gaacaattct tttaaggaaa     2460
atttagtttc atg tct cac att gat gat ctt gca cag ctc ggc act tcc         2509
           Met Ser His Ile Asp Asp Leu Ala Gln Leu Gly Thr Ser
             1               5                  10 act tgg ctc gac gac ctc tcc cgc gag cgc att act tcc ggc aat ctc         2557
Thr Trp Leu Asp Asp Leu Ser Arg Glu Arg Ile Thr Ser Gly Asn Leu
         15                  20                  25 agc cag gtt att gag gaa aag tct gta gtc ggt gtc acc acc aac cca         2605
Ser Gln Val Ile Glu Glu Lys Ser Val Val Gly Val Thr Thr Asn Pro
 30                  35                  40                  45
```

```
gct att ttc gca gca gca atg tcc aag ggc gat tcc tac gac gct cag    2653
Ala Ile Phe Ala Ala Ala Met Ser Lys Gly Asp Ser Tyr Asp Ala Gln
            50                  55                  60 atc gca gag ctc aag gcc gct ggc gca tct gtt gac cag gct gtt tac    2701
Ile Ala Glu Leu Lys Ala Ala Gly Ala Ser Val Asp Gln Ala Val Tyr
        65                  70                  75 gcc atg agc atc gac gac gtt cgc aat gct tgt gat ctg ttc acc ggc    2749
Ala Met Ser Ile Asp Asp Val Arg Asn Ala Cys Asp Leu Phe Thr Gly
                80                  85                  90 atc ttc gag tcc tcc aac ggc tac gac ggc cgc gtg tcc atc gag gtt    2797
Ile Phe Glu Ser Ser Asn Gly Tyr Asp Gly Arg Val Ser Ile Glu Val
            95                  100                 105 gac cca cgt atc tct gct gac cgc gac gca acc ctg gct cag gcc aag    2845
Asp Pro Arg Ile Ser Ala Asp Arg Asp Ala Thr Leu Ala Gln Ala Lys
110                 115                 120                 125 gag ctg tgg gca aag gtt gat cgt cca aac gtc atg atc aag atc cct    2893
Glu Leu Trp Ala Lys Val Asp Arg Pro Asn Val Met Ile Lys Ile Pro
                130                 135                 140 gca acc cca ggt tct ttg cca gca atc acc gac gct ttg gct gag ggc    2941
Ala Thr Pro Gly Ser Leu Pro Ala Ile Thr Asp Ala Leu Ala Glu Gly
            145                 150                 155 atc agc gtt aac gtc acc ttg atc ttc tcc gtt gct cgc tac cgc gag    2989
Ile Ser Val Asn Val Thr Leu Ile Phe Ser Val Ala Arg Tyr Arg Glu
        160                 165                 170 gtc atc gct gcg ttc atc gag ggc atc aag cag gct gct gca aac ggc    3037
Val Ile Ala Ala Phe Ile Glu Gly Ile Lys Gln Ala Ala Ala Asn Gly
    175                 180                 185 cac gac gtc tcc aag atc cac tct gtg gct tcc ttc ttc gtc tcc cgc    3085
His Asp Val Ser Lys Ile His Ser Val Ala Ser Phe Phe Val Ser Arg
190                 195                 200                 205 gtc gac gtt gag atc gac aag cgc ctc gag gca atc gga tcc gat gag    3133
Val Asp Val Glu Ile Asp Lys Arg Leu Glu Ala Ile Gly Ser Asp Glu
                210                 215                 220 gct ttg gct ctg cgc ggc aag gca ggc gtt gcc aac gct cag cgc gct    3181
Ala Leu Ala Leu Arg Gly Lys Ala Gly Val Ala Asn Ala Gln Arg Ala
            225                 230                 235 tac gct gtg tac aag gag ctt ttc gac gcc gcc gag ctg cct gaa ggt    3229
Tyr Ala Val Tyr Lys Glu Leu Phe Asp Ala Ala Glu Leu Pro Glu Gly
        240                 245                 250 gcc aac act cag cgc cca ctg tgg gca tcc acc ggc gtg aag aac cct    3277
Ala Asn Thr Gln Arg Pro Leu Trp Ala Ser Thr Gly Val Lys Asn Pro
    255                 260                 265 gcg tac gct gca act ctt tac gtt tcc gag ctg gct ggt cca aac acc    3325
Ala Tyr Ala Ala Thr Leu Tyr Val Ser Glu Leu Ala Gly Pro Asn Thr
270                 275                 280                 285 gtc aac acc atg cca gaa ggc acc atc gac gcg gtt ctg gag cag ggc    3373
Val Asn Thr Met Pro Glu Gly Thr Ile Asp Ala Val Leu Glu Gln Gly
                290                 295                 300 aac ctg cac ggt gac acc ctg tcc aac tcc gcg gca gaa gct gac gct    3421
Asn Leu His Gly Asp Thr Leu Ser Asn Ser Ala Ala Glu Ala Asp Ala
            305                 310                 315 gtg ttc tcc cag ctt gag gct ctg ggc gtt gac ttg gca gat gtc ttc    3469
Val Phe Ser Gln Leu Glu Ala Leu Gly Val Asp Leu Ala Asp Val Phe
        320                 325                 330 cag gtc ctg gag acc gag ggt gtg gac aag ttc gtt gct tct tgg agc    3517
Gln Val Leu Glu Thr Glu Gly Val Asp Lys Phe Val Ala Ser Trp Ser
    335                 340                 345 gaa ctg ctt gag tcc atg gaa gct cgc ctg aag tagaatcagc acgctgcatc   3570
Glu Leu Leu Glu Ser Met Glu Ala Arg Leu Lys
350                 355                 360
```

```
agtaacggcg acatgaaatc gaattagttc gatcttatgt ggccgttaca catctttcat      3630
taaagaaagg atcgtgacac taccatcgtg agcacaaaca cgaccccctc cagctggaca      3690
aacccactgc gcgacccgca ggataaacga ctcccccgca tcgctggccc ttccggcatg      3750
gtgatcttcg gtgtcactgg cgacttggct cgaaagaagc tgctccccgc catttatgat      3810
ctagcaaacc gcggattgct gcccccagga ttctcgttgg taggttacgg ccgccgcgaa      3870
tggtccaaag aagactttga aaaatacgta cgcgatgccg caagtgctgg tgctcgtacg      3930
gaattccgtg aaaatgtttg ggagcgcctc gccgagggta tggaatttgt tcgcggcaac      3990
tttgatgatg atgcagcttt cgacaacctc gctgcaacac tcaagcgcat cgacaaaacc      4050
cgcggcaccg ccggcaactg ggcttactac ctgtccattc caccagattc cttcacagcg      4110
gtctgccacc agctggagcg ttccggcatg gctgaatcca ccgaagaagc atggcgccgc      4170
gtgatcatcg agaagccttt cggccacaac ctcgaatccg cacacgagct caaccagctg      4230
gtcaacgcag tcttcccaga atcttctgtg ttccgcatcg accactattt gggcaaggaa      4290
acagttcaaa acatcctggc tctgcgtttt gctaaccagc tgtttgagcc actgtggaac      4350
tccaactacg ttgaccacgt ccagatcacc atggctgaag atattggctt gggtggacgt      4410
gctggttact acgacggcat cggcgcagcc cgcgacgtca tccagaacca cctgatccag      4470
ctcttggctc tggttgccat ggaagaacca atttcttttcg tgccagcgca gctgcaggca      4530
gaaaagatca aggtgctctc tgcgacaaag ccgtgctacc cattggataa aacctccgct      4590
cgtggtcagt acgctgccgg ttggcagggc tctgagttag tcaagggact cgcgaagaa      4650 gatggcttca accctgagtc caccactgag acttttgcgg cttgtacctt agagatcacg      4710
tctcgtcgct gggctggtgt gccgttctac ctgcgcaccg gtaagcgtct tggtcgccgt      4770
gttactgaga ttgccgtggt gtttaaagac gcaccacacc agcctttcga cggcgacatg      4830
actgtatccc ttggccaaaa cgccatcgtg attcgcgtgc agcctgatga aggtgtgctc      4890
atccgcttcg gttccaaggt tccaggttct gccatggaag tccgtgacgt caacatggac      4950
ttctcctact cagaatcctt cactgaagaa tcacctgaag catacgagcg cctcattttg      5010
gatgcgctgt tagatgaatc cagcctcttc cctaccaacg aggaagtgga actgagctgg      5070
aagattctgg atccaattct tgaagcatgg gatgccgatg gagaaccaga ggattaccca      5130
gcgggtacgt ggggtccaaa gagcgctgat gaaatgcttt cccgcaacgg tcacacctgg      5190
cgcaggccat aatttagggg caaaaaatga tctttgaact tccggatacc accacccagc      5250
aaatttccaa gaccctaact cgactgcgtg aatcgggcac ccaggtcacc accggccgag      5310
tgctcaccct catcgtggtc actgactccg aaagcgatgt cgctgcagtt accgagtcca      5370
ccaatgaagc ctcgcgcgag cacccatctc gcgtgatcat tttggtggtt ggcgataaaa      5430
ctgcagaaaa caaagttgac gcagaagtcc gtatcggtgg cgacgctggt gcttccgaga      5490
tgatcatcat gcatctcaac ggacctgtcg ctgacaagct ccagtatgtc gtcacaccac      5550
tgttgcttcc tgacaccccc atcgttgctt ggtggccagg tgaatcacca aagaatcctt      5610
cccaggaccc aattggacgc atcgcacaac gacgcatcac tgatgctttg tacgaccgtg      5670
atgacgcact agaagatcgt gttgagaact atcacccagg tgataccgac atgacgtggg      5730
cgcgccttac ccagtggcgg ggacttgttg cctcctcatt ggatcaccca ccacacagcg      5790
aaatcacttc cgtgaggctg accggtgcaa gcggcagtac ctcggtggat ttggctgcag      5850
gctggttggc gcggaggctg aaagtgcctg tgatccgcga ggtgcagat gctcccaccg      5910 tgccaaccga tgagtttggt actccactgc tggctatcca gcgcctggag atcgttcgca      5970
```

-continued

```
ccaccggctc gatcatcatc accatctatg acgctcatac ccttcaggta gagatgccgg    6030
aatccggcaa tgccccatcg ctggtggcta ttggtcgtcg aagtgagtcc gactgcttgt    6090
ctgaggagct tcgccacatg gatccagatt tgggctacca gcacgcacta tccggcttgt    6150
ccagcgtcaa gctggaaacc gtctaaggag aaatacaaca ctatggttga tgtagtacgc    6210
gcacgcgata ctgaagattt ggttgcacag gctgcctcca aattcattga ggttgttgaa    6270
gcagcaactg ccaataatgg caccgcacag gtagtgctca ccggtggtgg cgccggcatc    6330
aagttgctgg aaaagctcag cgttgatgcg gctgaccttg cctgggatcg cattcatgtg    6390
ttcttcggcg atgagcgcaa tgtccctgtc agtgattctg agtccaatga gggccaggct    6450
cgtgaggcac tgttgtccaa ggtttctatc cctgaagcca acattcacgg atatggtctc    6510
ggcgacgtag atcttgcaga ggcagcccgc gcttacgaag ctgtgttgga tgaattcgca    6570
ccaaacggct ttgatcttca cctgctcggc atgggtggcg aaggccatat caactccctg    6630
ttccctcaca ccgatgcagt caaggaatcc tccgcaaagg tcatcgcggt gtttgattcc    6690
cctaagcctc cttcagagcg tgcaactcta acccttcctg cggttcactc cgcaaagcgc    6750
gtgtggttgc tggtttctgg tgcggagaag gctgaggcag ctgcggcgat cgtcaacggt    6810
gagcctgctg ttgagtggcc tgctgctgga gctaccggat ctgaggaaac ggtattgttc    6870
ttggctgatg atgctgcagg aaatctctaa gcagcgccag ctctaacaag aagctttaac    6930
aagaagctct aacgaaaagc actaacaaac taatccgggt gcgaaccttc atctgaatcg    6990
atgga                                                                6995
```

<210> SEQ ID NO 2
<211> LENGTH: 360
<212> TYPE: PRT
<213> ORGANISM: Corynebacterium glutamicum

<400> SEQUENCE: 2

```
Met Ser His Ile Asp Asp Leu Ala Gln Leu Gly Thr Ser Thr Trp Leu
 1               5                   10                  15

Asp Asp Leu Ser Arg Glu Arg Ile Thr Ser Gly Asn Leu Ser Gln Val
             20                  25                  30

Ile Glu Glu Lys Ser Val Val Gly Val Thr Thr Asn Pro Ala Ile Phe
         35                  40                  45

Ala Ala Ala Met Ser Lys Gly Asp Ser Tyr Asp Ala Gln Ile Ala Glu
     50                  55                  60

Leu Lys Ala Ala Gly Ala Ser Val Asp Gln Ala Val Tyr Ala Met Ser
 65                  70                  75                  80

Ile Asp Asp Val Arg Asn Ala Cys Asp Leu Phe Thr Gly Ile Phe Glu
                 85                  90                  95

Ser Ser Asn Gly Tyr Asp Gly Arg Val Ser Ile Glu Val Asp Pro Arg
            100                 105                 110

Ile Ser Ala Asp Arg Asp Ala Thr Leu Ala Gln Ala Lys Glu Leu Trp
        115                 120                 125

Ala Lys Val Asp Arg Pro Asn Val Met Ile Lys Ile Pro Ala Thr Pro
    130                 135                 140

Gly Ser Leu Pro Ala Ile Thr Asp Ala Leu Ala Glu Gly Ile Ser Val
145                 150                 155                 160

Asn Val Thr Leu Ile Phe Ser Val Ala Arg Tyr Arg Glu Val Ile Ala
                165                 170                 175

Ala Phe Ile Glu Gly Ile Lys Gln Ala Ala Ala Asn Gly His Asp Val
            180                 185                 190
```

```
Ser Lys Ile His Ser Val Ala Ser Phe Phe Val Ser Arg Val Asp Val
        195                 200                 205

Glu Ile Asp Lys Arg Leu Glu Ala Ile Gly Ser Asp Glu Ala Leu Ala
    210                 215                 220

Leu Arg Gly Lys Ala Gly Val Ala Asn Ala Gln Arg Ala Tyr Ala Val
225                 230                 235                 240

Tyr Lys Glu Leu Phe Asp Ala Ala Glu Leu Pro Glu Gly Ala Asn Thr
                245                 250                 255

Gln Arg Pro Leu Trp Ala Ser Thr Gly Val Lys Asn Pro Ala Tyr Ala
            260                 265                 270

Ala Thr Leu Tyr Val Ser Glu Leu Ala Gly Pro Asn Thr Val Asn Thr
        275                 280                 285

Met Pro Glu Gly Thr Ile Asp Ala Val Leu Glu Gln Gly Asn Leu His
    290                 295                 300

Gly Asp Thr Leu Ser Asn Ser Ala Ala Glu Ala Asp Ala Val Phe Ser
305                 310                 315                 320

Gln Leu Glu Ala Leu Gly Val Asp Leu Ala Asp Val Phe Gln Val Leu
                325                 330                 335

Glu Thr Glu Gly Val Asp Lys Phe Val Ala Ser Trp Ser Glu Leu Leu
            340                 345                 350

Glu Ser Met Glu Ala Arg Leu Lys
        355                 360

<210> SEQ ID NO 3
<211> LENGTH: 1083
<212> TYPE: DNA
<213> ORGANISM: Corynebacterium glutamicum
<220> FEATURE:
<221> NAME/KEY: CDS
<222> LOCATION: (1)..(1080)
<223> OTHER INFORMATION: tal

<400> SEQUENCE: 3 atg tct cac att gat gat ctt gca cag ctc ggc act tcc act tgg ctc     48
Met Ser His Ile Asp Asp Leu Ala Gln Leu Gly Thr Ser Thr Trp Leu
  1               5                  10                  15 gac gac ctc tcc cgc gag cgc att act tcc ggc aat ctc agc cag gtt     96
Asp Asp Leu Ser Arg Glu Arg Ile Thr Ser Gly Asn Leu Ser Gln Val
             20                  25                  30 att gag gaa aag tct gta gtc ggt gtc acc acc aac cca gct att ttc    144
Ile Glu Glu Lys Ser Val Val Gly Val Thr Thr Asn Pro Ala Ile Phe
         35                  40                  45 gca gca gca atg tcc aag ggc gat tcc tac gac gct cag atc gca gag    192
Ala Ala Ala Met Ser Lys Gly Asp Ser Tyr Asp Ala Gln Ile Ala Glu
     50                  55                  60 ctc aag gcc gct ggc gca tct gtt gac cag gct gtt tac gcc atg agc    240
Leu Lys Ala Ala Gly Ala Ser Val Asp Gln Ala Val Tyr Ala Met Ser
 65                  70                  75                  80 atc gac gac gtt cgc aat gct tgt gat ctg ttc acc ggc atc ttc gag    288
Ile Asp Asp Val Arg Asn Ala Cys Asp Leu Phe Thr Gly Ile Phe Glu
                 85                  90                  95 tcc tcc aac ggc tac gac ggc cgc gtg tcc atc gag gtt gac cca cgt    336
Ser Ser Asn Gly Tyr Asp Gly Arg Val Ser Ile Glu Val Asp Pro Arg
            100                 105                 110 atc tct gct gac cgc gac gca acc ctg gct cag gcc aag gag ctg tgg    384
Ile Ser Ala Asp Arg Asp Ala Thr Leu Ala Gln Ala Lys Glu Leu Trp
        115                 120                 125 gca aag gtt gat cgt cca aac gtc atg atc aag atc cct gca acc cca    432
Ala Lys Val Asp Arg Pro Asn Val Met Ile Lys Ile Pro Ala Thr Pro
    130                 135                 140
```

```
ggt tct ttg cca gca atc acc gac gct ttg gct gag ggc atc agc gtt       480
Gly Ser Leu Pro Ala Ile Thr Asp Ala Leu Ala Glu Gly Ile Ser Val
145                 150                 155                 160 aac gtc acc ttg atc ttc tcc gtt gct cgc tac cgc gag gtc atc gct       528
Asn Val Thr Leu Ile Phe Ser Val Ala Arg Tyr Arg Glu Val Ile Ala
                165                 170                 175 gcg ttc atc gag ggc atc aag cag gct gct gca aac ggc cac gac gtc       576
Ala Phe Ile Glu Gly Ile Lys Gln Ala Ala Ala Asn Gly His Asp Val
            180                 185                 190 tcc aag atc cac tct gtg gct tcc ttc ttc gtc tcc cgc gtc gac gtt       624
Ser Lys Ile His Ser Val Ala Ser Phe Phe Val Ser Arg Val Asp Val
        195                 200                 205 gag atc gac aag cgc ctc gag gca atc gga tcc gat gag gct ttg gct       672
Glu Ile Asp Lys Arg Leu Glu Ala Ile Gly Ser Asp Glu Ala Leu Ala
    210                 215                 220 ctg cgc ggc aag gca ggc gtt gcc aac gct cag cgc gct tac gct gtg       720
Leu Arg Gly Lys Ala Gly Val Ala Asn Ala Gln Arg Ala Tyr Ala Val
225                 230                 235                 240 tac aag gag ctt ttc gac gcc gcc gag ctg cct gaa ggt gcc aac act       768
Tyr Lys Glu Leu Phe Asp Ala Ala Glu Leu Pro Glu Gly Ala Asn Thr
                245                 250                 255 cag cgc cca ctg tgg gca tcc acc ggc gtg aag aac cct gcg tac gct       816
Gln Arg Pro Leu Trp Ala Ser Thr Gly Val Lys Asn Pro Ala Tyr Ala
            260                 265                 270 gca act ctt tac gtt tcc gag ctg gct ggt cca aac acc gtc aac acc       864
Ala Thr Leu Tyr Val Ser Glu Leu Ala Gly Pro Asn Thr Val Asn Thr
        275                 280                 285 atg cca gaa ggc acc atc gac gcg gtt ctg gag cag ggc aac ctg cac       912
Met Pro Glu Gly Thr Ile Asp Ala Val Leu Glu Gln Gly Asn Leu His
    290                 295                 300 ggt gac acc ctg tcc aac tcc gcg gca gaa gct gac gct gtg ttc tcc       960
Gly Asp Thr Leu Ser Asn Ser Ala Ala Glu Ala Asp Ala Val Phe Ser
305                 310                 315                 320 cag ctt gag gct ctg ggc gtt gac ttg gca gat gtc ttc cag gtc ctg      1008
Gln Leu Glu Ala Leu Gly Val Asp Leu Ala Asp Val Phe Gln Val Leu
                325                 330                 335 gag acc gag ggt gtg gac aag ttc gtt gct tct tgg agc gaa ctg ctt      1056
Glu Thr Glu Gly Val Asp Lys Phe Val Ala Ser Trp Ser Glu Leu Leu
            340                 345                 350 gag tcc atg gaa gct cgc ctg aag tag                                   1083
Glu Ser Met Glu Ala Arg Leu Lys
        355                 360

<210> SEQ ID NO 4
<211> LENGTH: 360
<212> TYPE: PRT
<213> ORGANISM: Corynebacterium glutamicum

<400> SEQUENCE: 4

Met Ser His Ile Asp Asp Leu Ala Gln Leu Gly Thr Ser Thr Trp Leu
1               5                   10                  15

Asp Asp Leu Ser Arg Glu Arg Ile Thr Ser Gly Asn Leu Ser Gln Val
            20                  25                  30

Ile Glu Glu Lys Ser Val Val Gly Val Thr Thr Asn Pro Ala Ile Phe
        35                  40                  45

Ala Ala Ala Met Ser Lys Gly Asp Ser Tyr Asp Ala Gln Ile Ala Glu
    50                  55                  60

Leu Lys Ala Ala Gly Ala Ser Val Asp Gln Ala Val Tyr Ala Met Ser
65                  70                  75                  80
```

```
Ile Asp Asp Val Arg Asn Ala Cys Asp Leu Phe Thr Gly Ile Phe Glu
             85                  90                  95

Ser Ser Asn Gly Tyr Asp Gly Arg Val Ser Ile Glu Val Asp Pro Arg
        100                 105                 110

Ile Ser Ala Asp Arg Asp Ala Thr Leu Ala Gln Ala Lys Glu Leu Trp
        115                 120                 125

Ala Lys Val Asp Arg Pro Asn Val Met Ile Lys Ile Pro Ala Thr Pro
130                 135                 140

Gly Ser Leu Pro Ala Ile Thr Asp Ala Leu Ala Gly Ile Ser Val
145                 150                 155                 160

Asn Val Thr Leu Ile Phe Ser Val Ala Arg Tyr Arg Glu Val Ile Ala
                165                 170                 175

Ala Phe Ile Glu Gly Ile Lys Gln Ala Ala Asn Gly His Asp Val
                180                 185                 190

Ser Lys Ile His Ser Val Ala Ser Phe Phe Val Ser Arg Val Asp Val
            195                 200                 205

Glu Ile Asp Lys Arg Leu Glu Ala Ile Gly Ser Asp Glu Ala Leu Ala
210                 215                 220

Leu Arg Gly Lys Ala Gly Val Ala Asn Ala Gln Arg Ala Tyr Ala Val
225                 230                 235                 240

Tyr Lys Glu Leu Phe Asp Ala Ala Glu Leu Pro Glu Gly Ala Asn Thr
                245                 250                 255

Gln Arg Pro Leu Trp Ala Ser Thr Gly Val Lys Asn Pro Ala Tyr Ala
                260                 265                 270

Ala Thr Leu Tyr Val Ser Glu Leu Ala Gly Pro Asn Thr Val Asn Thr
                275                 280                 285

Met Pro Glu Gly Thr Ile Asp Ala Val Leu Gln Gly Asn Leu His
290                 295                 300

Gly Asp Thr Leu Ser Asn Ser Ala Ala Glu Ala Asp Ala Val Phe Ser
305                 310                 315                 320

Gln Leu Glu Ala Leu Gly Val Asp Leu Ala Asp Val Phe Gln Val Leu
                325                 330                 335

Glu Thr Glu Gly Val Asp Lys Phe Val Ala Ser Trp Ser Glu Leu Leu
                340                 345                 350

Glu Ser Met Glu Ala Arg Leu Lys
        355                 360

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 5
ggtacaaagg gtcttaag                                              18

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 6
gatttcatgt cgccgtta                                              18
```

PROCESS FOR THE PREPARATION OF L-AMINO ACIDS BY OVEREXPRESSING THE TAL GENE ENCODING TRANSALDOLASE

CROSS REFERENCE TO RELATED APPLICATIONS

This is a divisional application of U.S. patent application Ser. No. 09/531,266, filed Mar. 20, 2000, which issued as U.S. Pat. No. 6,797,509 B1 on Sep. 28, 2004, which claims priority to U.S. Provisional Patent Appl. No. 60/142,915 filed Jul. 9, 1999.

The invention provides nucleotide sequences which code for the tal gene and a process for the fermentative preparation of amino acids, in particular L-lysine, L-threonine, L-isoleucine and L-tryptophan, using coryneform bacteria in which the tal gene is amplified.

PRIOR ART

Amino acids, in particular L-lysine, are used in human medicine and in the pharmaceuticals industry, but in particular in animal nutrition.

It is known that amino acids are prepared by fermentation by strains of coryneform bacteria, in particular *Corynebacterium glutamicum*. Because of their great importance, work is constantly being undertaken to improve the preparation processes. Improvements to the processes can relate to fermentation measures, such as e.g. stirring and supply of oxygen, or the composition of the nutrient media, such as e.g. the sugar concentration during the fermentation, or the working up to the product form by e.g. ion exchange chromatography, or the intrinsic output properties of the microorganism itself.

Methods of mutagenesis, selection and mutant selection are used to improve the output properties of these microorganisms. Strains which are resistant to antimetabolites, such as e.g. the lysine analogue S-(2-aminoethyl)-cysteine, or are auxotrophic for metabolites of regulatory importance and produce L-amino acids, such as e.g. L-lysine, are obtained in this manner.

Methods of the recombinant DNA technique have also been employed for some years for improving the strain of *Corynebacterium* strains which produce amino acids, by amplifying individual amino acid biosynthesis genes and investigating the effect on the amino acid production. Review articles in this context are to be found, inter alia, in Kinoshita ("Glutamic Acid Bacteria", in: Biology of Industrial Microorganisms, Demain and Solomon (Eds.), Benjamin Cummings, London, UK, 1985, 115-142), Hilliger (BioTec 2, 40-44 (1991)), Eggeling (Amino Acids 6:261-272 (1994)), Jetten and Sinskey (Critical Reviews in Biotechnology 15, 73-103 (1995)) and Sahm et al. (Annuals of the New York Academy of Science 782, 25-39 (1996)).

The importance of the pentose phosphate cycle for the biosynthesis and production of amino acids, in particular L-lysine, by coryneform bacteria is the subject of numerous efforts among experts.

Thus Oishi and Aida (Agricultural and Biological Chemistry 29, 83-89 (1965)) report on the "hexose monophosphate shunt" of *Brevibacterium* ammoniagenes. Sugimoto and Shio (Agricultural and Biological [sic] Chemistry 51, 101-108 (1987)) report on the regulation of glucose 6-phosphate dehydrogenase in *Brevibacterium flavum*.

OBJECT OF THE INVENTION

The inventors had the object of providing new measures for improved fermentative preparation of amino acids, in particular L-lysine, L-threonine, L-isoleucine and L-tryptophan.

DESCRIPTION OF THE INVENTION

Amino acids, in particular L-lysine, are used in human medicine, in the pharmaceuticals industry and in particular in animal nutrition. There is therefore a general interest in providing new improved processes for the preparation of amino acids, in particular L-lysine.

When L-lysine or lysine are mentioned in the following, not only the base but also the salts, such as e.g. lysine monohydrochloride or lysine sulfate, are also meant by this.

The invention provides an isolated polynucleotide from coryneform bacteria, comprising a polynucleotide sequence chosen from the group consisting of a) polynucleotide which is identical to the extent of at least 70% to a polynucleotide which codes for a polypeptide which comprises the amino acid sequences of SEQ ID NO. 2 or SEQ ID NO. 4,
b) polynucleotide which codes for a polypeptide which comprises an amino acid sequence which is identical to the extent of at least 70% to the amino acid sequences of SEQ ID NO. 2 or SEQ ID NO. 4,
c) polynucleotide which is complementary to the polynucleotides of a) or b) and
d) polynucleotide comprising at least 15 successive nucleotides of the polynucleotide sequence of a), b) or c).

The invention also provides the polynucleotide as claimed in claim 1, this preferably being a DNA which is capable of replication, comprising:

(i) a nucleotide sequence chosen from the group consisting of SEQ ID NO. 1 and SEQ ID NO. 3 or
(ii) at least one sequence which corresponds to sequence (i) within the range of the degeneration of the genetic code, or
(iii) at least one sequence which hybridizes with the sequence complementary to sequence (i) or (ii), and optionally
(iv) sense mutations of neutral function in (i).

The invention also provides
a polynucleotide as claimed in claim 4, comprising one of the nucleotide sequences as shown in SEQ ID NO. 1 and SEQ ID NO. 3,
a polynucleotide as claimed in claim 5, which codes for a polypeptide which comprises the amino acid sequence as shown in SEQ ID NO. 2 and SEQ ID NO. 4,
a vector containing the polynucleotide as claimed in claim 1, and coryneform bacteria, serving as the host cell, which contain the vector.

The invention also provides polynucleotides which substantially comprise a polynucleotide sequence, which are [sic] obtainable by screening by means of hybridization of a corresponding gene library, which comprises the complete gene with the polynucleotide sequence corresponding to SEQ ID NO. 1 or SEQ ID NO. 3, with a probe which comprises the sequence of the polynucleotide mentioned, according to SEQ ID NO. 1 or SEQ ID NO. 3 or a fragment thereof, and isolation of the DNA sequence mentioned.

Polynucleotide sequences according to the invention are suitable as hybridization probes for RNA, cDNA and DNA, in order to isolate, in the full length, cDNA which code for transaldolase and to isolate those cDNA or genes which have a high similarity of sequence with that of the transaldolase gene.

Polynucleotide sequences according to the invention are furthermore suitable as primers for the preparation of DNA of genes which code for transaldolase by the polymerase chain reaction (PCR).

Such oligonucleotides which serve as probes or primers comprise at least 30, preferably at least 20, especially preferably at least 15 successive nucleotides. Oligonucleotides which have a length of at least 40 or 50 nucleotides are also suitable.

"Isolated" means separated out of its natural environment.

"Polynucleotide" in general relates to polyribonucleotides and polydeoxyribonucleotides, it being possible for these to be non-modified RNA or DNA or modified RNA or DNA.

"Polypeptides" is understood as meaning peptides or proteins which comprise two or more amino acids bonded via peptide bonds.

The polypeptides according to the invention include a polypeptide according to SEQ ID NO. 2 or SEQ ID NO. 4, in particular those with the biological activity of transaldolase, and also those which are identical to the extent of at least 70% to the polypeptide according to SEQ ID NO. 2 or SEQ ID NO. 4, and preferably are identical to the extent of at least 80% and in particular to the extent of at least 90% to 95% to the polypeptide according to SEQ ID NO. 2 or SEQ ID NO. 4, and have the activity mentioned.

The invention also provides a process for the fermentative preparation of amino acids, in particular L-lysine, L-threonine, L-isoleucine and L-tryptophan, using coryneform bacteria which in particular already produce an amino acid, and in which the nucleotide sequences which code for the tal gene are amplified, in particular over-expressed.

The term "amplification" in this connection describes the increase in the intracellular activity of one or more enzymes in a microorganism which are coded by the corresponding DNA, for example by increasing the number of copies of the gene or genes, using a potent promoter or using a gene which codes for a corresponding enzyme having a high activity, and optionally combining these measures.

The microorganisms which the present invention provides can prepare L-amino acids, in particular L-lysine, from glucose, sucrose, lactose, fructose, maltose, molasses, starch, cellulose or from glycerol and ethanol. They can be representatives of coryneform bacteria, in particular of the genus *Corynebacterium*. Of the genus *Corynebacterium*, there may be mentioned in particular the species *Corynebacterium glutamicum*, which is known among experts for its ability to produce L-amino acids.

Suitable strains of the genus *Corynebacterium*, in particular of the species *Corynebacterium glutamicum*, are, for example, the known wild-type strains

*Corynebacterium glutamicum* ATCC13032
*Corynebacterium acetoglutamicum* ATCC15806
*Corynebacterium acetoacidophilum* ATCC13870
*Corynebacterium thermoaminogenes* FERM BP-1539
*Corynebacterium melassecola* ATCC17965
*Brevibacterium flavum* ATCC14067
*Brevibacterium lactofermentum* ATCC13869 and
*Brevibacterium divaricatum* ATCC14020 and L-lysine-producing mutants or strains prepared therefrom, such as, for example

*Corynebacterium glutamicum* FERM-P 1709
*Brevibacterium flavum* FERM-P 1708
*Brevibacterium lactofermentum* FERM-P 1712
*Corynebacterium glutamicum* FERM-P 6463
*Corynebacterium glutamicum* FERM-P 6464 and
*Corynebacterium glutamicum* ATCC13032
*Corynebacterium glutamicum* DM58-1
*Corynebacterium glutamicum* DSM12866.

and L-threonine-producing mutants or strains prepared therefrom, such as, for example

*Corynebacterium glutamicum* ATCC21649
*Brevibacterium flavum* BB69
*Brevibacterium flavum* DSM5399
*Brevibacterium lactofermentum* FERM-BP 269
*Brevibacterium lactofermentum* TBB-10 and L-isoleucine-producing mutants or strains prepared therefrom, such as, for example

*Corynebacterium glutamicum* ATCC 14309
*Corynebacterium glutamicum* ATCC 14310
*Corynebacterium glutamicum* ATCC 14311
*Corynebacterium glutamicum* ATCC 15168
*Corynebacterium ammoniagenes* ATCC 6871 and L-tryptophan-producing mutants or strains prepared therefrom, such as, for example

*Corynebacterium glutamicum* ATCC21850 and
*Corynebacterium glutamicum* KY9218 (pKW9901)

The inventors have succeeded in isolating the new tal gene of *C. glutamicum* which codes for transaldolase (EC 2.2.1.2).

To isolate the tal gene or also other genes of *C. glutamicum*, a gene library of this microorganism is first set up in *E. coli*. The setting up of gene libraries is described in generally known textbooks and handbooks. The textbook by Winnacker: Gene und Klone, Eine Einführung in die Gentechnologie [Genes and Clones, An Introduction to Genetic Engineering] (Verlag Chemie, Weinheim, Germany, 1990) or the handbook by Sambrook et al.: Molecular Cloning, A Laboratory Manual (Cold Spring Harbor Laboratory Press, 1989) may be mentioned as an example. A well-known gene library is that of the *E. coli* K-12 strain W3110 set up in λ vectors by Kohara et al. (Cell 50, 495-508 (1987)). Bathe et al. (Molecular and General Genetics, 252:255-265, 1996) describe a gene library of *C. glutamicum* ATCC13032, which was set up with the aid of the cosmid vector SuperCos I (Wahl et al., 1987, Proceedings of the National Academy of Sciences USA, 84:2160-2164) in the *E. coli* K-12 strain NM554 (Raleigh et al., 1988, Nucleic Acids Research 16:1563-1575). Börmann et al. (Molecular Microbiology 6(3), 317-326)) (1992)) in turn describe a gene library of *C. glutamicum* ATCC13032 using the cosmid pHC79 (Hohn and Collins, Gene 11, 291-298 (1980)). O'Donohue (The Cloning and Molecular Analysis of Four Common Aromatic Amino Acid Biosynthetic Genes from *Corynebacterium glutamicum*. Ph.D. Thesis, National University of Ireland, Galway, 1997) describes the cloning of *C. glutamicum* genes using the λ Zap expression system described by Short et al. (Nucleic Acids Research, 16: 7583). To prepare a gene library of *C. glutamicum* in *E. coli* it is also possible to use plasmids such as pBR322 (Bolivar, Life Sciences, 25, 807-818 (1979)) or pUC9 (Vieira et al., 1982, Gene, 19:259-268). Suitable hosts are, in particular, those *E. coli* strains which are restriction- and recombination-defective. An example of these is the strain DH5αmcr, which has been described by Grant et al. (Proceedings of the National Academy of Sciences USA, 87 (1990) 4645-4649). The long DNA fragments cloned with the aid of cosmids can then in turn be subcloned and subsequently sequenced in the usual vectors which are suitable for sequencing, such as is described e.g. by Sanger et al. (Proceedings of the National Academy of Sciences of the United States of America, 74:5463-5467, 1977).

The DNA sequences obtained can then be investigated with known algorithms or sequence analysis programs, such as e.g. that of Staden (Nucleic Acids Research 14, 217-232 (1986)), the GCG program of Butler (Methods of Biochemical Analysis 39, 74-97 (1998)) the FASTA algorithm of Pearson and Lipman (Proceedings of the National Academy of Sciences USA 85, 2444-2448 (1988)) or the BLAST algorithm of Altschul et al. (Nature Genetics 6, 119-129 (1994)) and compared with the sequence entries which exist in databanks accessible to the public. Databanks for nucleotide sequences which are accessible to the public are, for example, that of the European Molecular Biologies Laboratories (EMBL, Heidelberg, Germany) of that of the National Center for Biotechnology Information (NCBI, Bethesda, Md., USA).

The invention provides the new DNA sequence from *C. glutamicum* which contains the DNA section which codes for the tal gene, shown as SEQ ID NO 1 and SEQ ID NO 3. The amino acid sequence of the corresponding protein has furthermore been derived from the present DNA sequence using the methods described above. The resulting amino acid sequence of the tal gene product is shown in SEQ ID NO 2 and SEQ ID NO 4.

A gene library produced in the manner described above can furthermore be investigated by hybridization with nucleotide probes of known sequence, such as, for example, the zwf gene (JP-A-09224661). The cloned DNA of the clones which show a positive reaction in the hybridization is sequenced in turn to give on the one hand the known nucleotide sequence of the probe employed and on the other hand the adjacent new DNA sequences.

Coding DNA sequences which result from SEQ ID NO 3 by the degeneracy of the genetic code are also a constituent of the invention. In the same way, DNA sequences which hybridize with SEQ ID NO 3 or parts of or [sic] SEQ ID NO 3 are a constituent of the invention. Conservative amino acid exchanges, such as e.g. exchange of glycine for alanine or of aspartic acid for glutamic acid in proteins, are furthermore known among experts as "sense mutations" which do not lead to a fundamental change in the activity of the protein, i.e. are of neutral function. It is furthermore known that changes on the N and/or C terminus of a protein cannot substantially impair or can even stabilize the function thereof. Information in this context can be found by the expert, inter alia, in Ben-Bassat et al. (Journal of Bacteriology 169:751-757 (1987)), in O'Regan et al. (Gene 77:237-251 (1989)), in Sahin-Toth et al. (Protein Sciences 3:240-247 (1994)), in Hochuli et al. (Bio/Technology 6:1321-1325 (1988)) and in known textbooks of genetics and molecular biology. Amino acid sequences which result in a corresponding manner from SEQ ID NO 2 or SEQ ID NO 4 are also a constituent of the invention.

In the same way, DNA sequences which hybridize with or [sic] SEQ ID NO 3 or parts of or [sic] SEQ ID NO 3 are a constituent of the invention. Finally, DNA sequences which are prepared by the polymerase chain reaction (PCR) using primers which result from SEQ ID NO 3 are a constituent of the invention. Such oligonucleotides typically have a length of at least 15 nucleotides.

Instructions for identifying DNA sequences by means of hybridization can be found by the expert, inter alia, in the handbook "The DIG System Users Guide for Filter Hybridization" from Boehringer Mannheim GmbH (Mannheim, Germany, 1993) and in Liebl et al. (International Journal of Systematic Bacteriology (1991) 41: 255-260). Instructions for amplification of DNA sequences with the aid of the polymerase chain reaction (PCR) can be found by the expert, inter alia, in the handbook by Gait: Oligonukleotide [sic] synthesis: a practical approach (IRL Press, Oxford, UK, 1984) and in Newton and Graham: PCR (Spektrum Akademischer Verlag, Heidelberg, Germany, 1994).

The inventors have found that coryneform bacteria produce amino acids in an improved manner after over-expression of the tal gene.

To achieve an over-expression, the number of copies of the corresponding genes can be increased, or the promoter and regulation region or the ribosome binding site upstream of the structural gene can be mutated. Expression cassettes which are incorporated upstream of the structural gene act in the same way. By inducible promoters, it is additionally possible to increase the expression in the course of fermentative L-amino acid production. The expression is likewise improved by measures to prolong the life of the m-RNA. Furthermore, the enzyme activity is also increased by preventing the degradation of the enzyme protein. The genes or gene constructs can either be present in plasmids with a varying number of copies, or can be integrated and amplified in the chromosome. Alternatively, an over-expression of the genes in question can furthermore be achieved by changing the composition of the media and the culture procedure.

Instructions in this context can be found by the expert, inter alia, in Martin et al. (Bio/Technology 5, 137-146 (1987)), in Guerrero et al. (Gene 138, 35-41 (1994)), Tsuchiya and Morinaga (Bio/Technology 6, 428-430 (1988)), in Eikmanns et al. (Gene 102, 93-98 (1991)), in European Patent Specification EPS 0 472 869, in U.S. Pat. No. 4,601,893, in Schwarzer and Pühler (Bio/Technology 9, 84-87 (1991)), in Reinscheid et al. (Applied and Environmental Microbiology 60, 126-132 (1994)), in LaBarre et al. (Journal of Bacteriology 175, 1001-1007 (1993)), in Patent Application WO 96/15246, in Malumbres et al. (Gene 134, 15-24 (1993)), in Japanese Laid-Open Specification JP-A-10-229891, in Jensen and Hammer (Biotechnology and Bioengineering 58, 191-195 (1998)), in Makrides (Microbiological Reviews 60:512-538 (1996)) and in known textbooks of genetics and molecular biology.

By way of example, the tal gene according to the invention was over-expressed with the aid of plasmids.

Suitable plasmids are those which are replicated in coryneform bacteria. Numerous known plasmid vectors, such as e.g. pZ1 (Menkel et al., Applied and Environmental Microbiology (1989) 64: 549-554), pEKEx1 (Eikmanns et al., Gene 102: 93-98 (1991)) or pHS2-1 (Sonnen et al., Gene 107:69-74 (1991)) are based on the cryptic plasmids pHM1519, pBL1 or pGA1. Other plasmid vectors, such as e.g. those based on pCG4 (U.S. Pat. No. 4,489,160), or pNG2 (Serwold-Davis et al., FEMS Microbiology Letters 66, 119-124 (1990)), or pAG1 (U.S. Pat. No. 5,158,891), can be used in the same manner.

Plasmid vectors which are furthermore suitable are also those with the aid of which the process of gene amplification by integration into the chromosome can be used, as has been described, for example, by Reinscheid et al. (Applied and Environmental Microbiology 60, 126-132 (1994)) for duplication or amplification of the hom-thrB operon. In this method, the complete gene is cloned in a plasmid vector which can replicate in a host (typically *E. coli*), but not in *C. glutamicum*. Possible vectors are, for example, pSUP301 (Simon et al., Bio/Technology 1, 784-791 (1983)), pK18mob or pK19mob (Schäfer et al., Gene 145, 69-73 (1994)), pGEM-T (Promega corporation, Madison, Wis., USA), pCR2.1-TOPO (Shuman (1994). [sic] Journal of Biological Chemistry 269: 32678-84; U.S. Pat. No. 5,487,993), PCR® Blunt (Invitrogen, Groningen, Holland; Bernard et al., Journal of Molecular Biology, 234: 534-541 (1993)), pEM1 (Schrumpf et al, 1991, Journal of Bacteriology 173:4510-4516) or pBGS8 (Spratt et al., 1986, Gene 41: 337-342). The plasmid vector which contains the gene to be amplified is then transferred into the desired strain of *C. glutamicum* by conjugation or transformation. The method of conjugation is described, for example, by Schäfer et al. (Applied and Environmental Microbiology 60, 756-759 (1994)). Methods for transformation are described, for example, by Thierbach et al. (Applied Microbiology and Biotechnology 29, 356-362 (1988)), Dunican and Shivnan (Bio/Technology 7, 1067-1070 (1989)) and Tauch et al. (FEMS Microbiological Letters 123, 343-347 (1994)). After homologous recombination by means of a "cross over" event, the resulting strain contains at least two copies of the gene in question.

Figure 1:
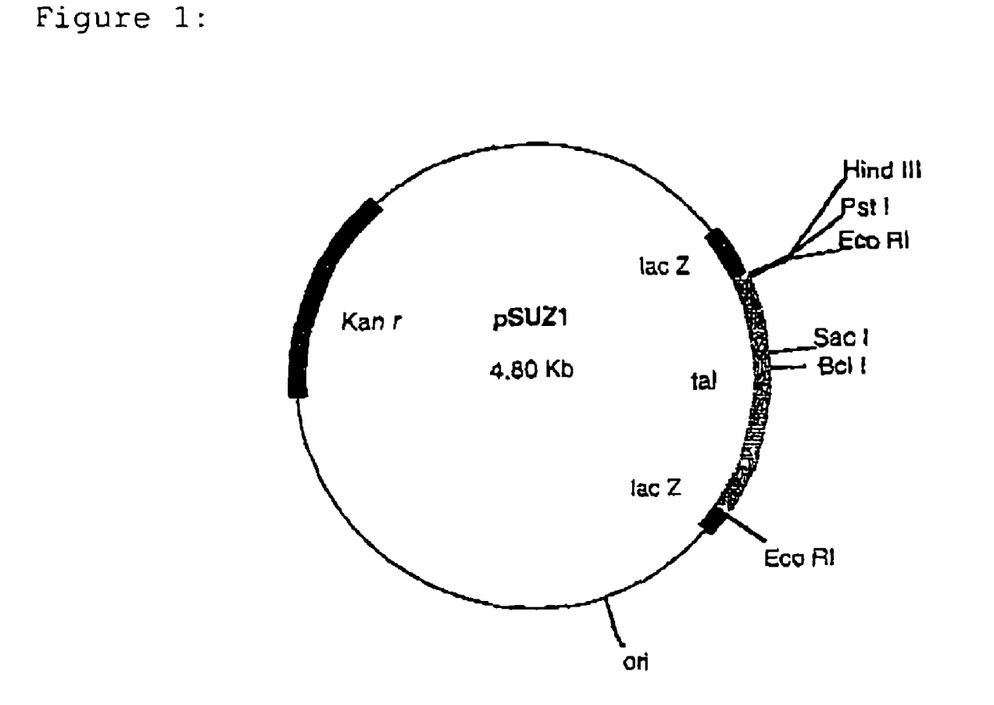
FIG. 1: Map of the plasmid pSUZ1

An example of a plasmid vector with the aid of which the process of amplification by integration can be carried out is pSUZ1, which is shown in FIG. 1. Plasmid pSUZ1 consists of the *E. coli* vector pBGS8 described by Spratt et al. (Gene 41: 337-342(1986)), into which the tal gene has been incorporated.

In addition, it may be advantageous for the production of amino acids to amplify or over-express one or more enzymes of the particular biosynthesis pathway, of glycolysis, of anaplerosis, of the pentose phosphate pathway or of amino acid export, in addition to the tal gene.

Thus, for example, for the preparation of L-amino acids, in particular L-lysine, one or more genes chosen from the group consisting of the dapA gene which codes for dihydrodipicolinate synthase (EP-B 0 197 335),
the lysC gene which codes for a feed back resistant aspartate kinase (Kalinowski et al. (1990), Molecular and General Genetics 224: 317-324),
the gap gene which codes for glycerolaldehyde 3-phosphate dehydrogenase (Eikmanns (1992), Journal of Bacteriology 174:6076-6086),
the pyc gene which codes for pyruvate carboxylase (DE-A-198 31 609),
the mqo gene which codes for malate:quinone oxidoreductase (Molenaar et al., European Journal of Biochemistry 254, 395-403 (1998)),
the tkt gene which codes for transketolase (accession number AB023377 of the databank of European Molecular Biologies Laboratories (EMBL, Heidelberg, Germany)),
the gnd gene which codes for 6-phosphogluconate dehydrogenase (JP-A-9-224662),
the zwf gene which codes for glucose 6-phosphate dehydrogenase (JP-A-9-224661),
the lysE gene which codes for lysine export (DE-A-195 48 222),
the zwa1 gene (DE 199 59 328.0; DSM 13115),
the eno gene which codes for enolase (DE: 19947791.4),
the devB gene,
the opcA gene (DSM 13264)
can be amplified, preferably over-expressed, at the same time.

Thus, for example, for the preparation of L-threonine, one or more genes chosen from the group consisting of at the same time the hom gene which codes for homoserine dehydrogenase (Peoples et al., Molecular Microbiology 2, 63-72 (1988)) or the hom$^{dr}$ allele which codes for a "feed back resistant" homoserine dehydrogenase (Archer et al., Gene 107, 53-59 (1991),
the gap gene which codes for glycerolaldehyde 3-phosphate dehydrogenase (Eikmanns (1992), Journal of Bacteriology 174:6076-6086),
the pyc gene which codes for pyruvate carboxylase (DE-A-198 31 609),
the mqo gene which codes for malate:quinone oxidoreductase (Molenaar et al., European Journal of Biochemistry 254, 395-403 (1998)),
the tkt gene which codes for transketolase (accession number AB023377 of the databank of European Molecular Biologies Laboratories (EMBL, Heidelberg, Germany)),
the gnd gene which codes for 6-phosphogluconate dehydrogenase (JP-A-9-224662),
the zwf gene which codes for glucose 6-phosphate dehydrogenase (JP-A-9-224661),
the thrE gene which codes for threonine export (DE 199 41 478.5; DSM 12840),
the zwa1 gene (DE 199 59 328.0; DSM 13115),
the eno gene which codes for enolase (DE: 19947791.4),
the devB gene,
the opcA gene (DSM 13264)
can be amplified, preferably over-expressed, at the same time . . . [sic]

It may furthermore be advantageous for the production of amino acids to attenuate the pck gene which codes for phosphoenol pyruvate carboxykinase (DE 199 50 409.1 DSM 13047) and/or
the pgi gene which codes for glucose 6-phosphate isomerase (U.S. Ser. No. 09/396,478, DSM 12969), or
the poxB gene which codes for pyruvate oxidase (DE 199 51 975.7; DSM 13114), or
the zwa2 gene (DE: 199 59 327.2; DSM 13113)
at the same time, in addition to the amplification of the tal gene.

In addition to over-expression of the tal gene it may furthermore be advantageous for the production of amino acids to eliminate undesirable side reactions (Nakayama: "Breeding of Amino Acid Producing Micro-organisms", in: Overproduction of Microbial Products, Krumphanzl, Sikyta, Vanek (eds.), Academic Press, London, UK, 1982).

The microorganisms prepared according to the invention can be cultured continuously or discontinuously in the batch process (batch culture) or in the fed batch (feed process) or repeated fed batch process (repetitive feed process) for the purpose of production of L-amino acids. A summary of known culture methods are [sic] described in the textbook by Chmiel (Bioprozeβtechnik 1. Einführung in die Bioverfahrenstechnik [Bioprocess Technology 1. Introduction to Bioprocess Technology (Gustav Fischer Verlag, Stuttgart, 1991)) or in the textbook by Storhas (Bioreaktoren und periphere Einrichtungen [Bioreactors and Peripheral Equipment] (Vieweg Verlag, Braunschweig/Wiesbaden, 1994)).

The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981). Sugars and carbohydrates, such as e.g. glucose, sucrose, lactose, fructose, maltose, molasses, starch and cellulose, oils and fats, such as e.g. soya oil, sunflower oil, groundnut oil and coconut fat, fatty acids, such as e.g. palmitic acid, stearic acid and linoleic acid, alcohols, such as e.g. glycerol and ethanol, and organic acids, such as e.g. acetic acid, can be used as the source of carbon. These substances can be used individually or as a mixture. Organic nitrogen-containing compounds, such as peptones, yeast extract, meat extract, malt extract, corn steep liquor, soya bean flour and urea, or inorganic compounds, such as ammonium sulphate, ammonium chloride, ammonium phosphate, ammonium carbonate and ammonium nitrate, can be used as the source of nitrogen. The sources of nitrogen can be used individually or as a mixture. Phosphoric acid, potassium dihydrogen phosphate or dipotassium hydrogen phosphate or the corresponding sodium-containing salts can be used as the source of phosphorus. The culture medium must furthermore comprise salts of metals, such as e.g. magnesium sulfate or iron sulfate, which are necessary for growth. Finally, essential growth substances, such as amino acids and vitamins, can be employed in addition to the abovementioned substances. Suitable precursors can moreover be added to the culture medium. The starting substances mentioned can be added to the culture in the form of a single batch, or can be fed in during the culture in a suitable manner.

Basic compounds, such as sodium hydroxide, potassium hydroxide, ammonia or aqueous ammonia, or acid compounds, such as phosphoric acid or sulfuric acid, can be employed in a suitable manner to control the pH of the culture. Antifoams, such as e.g. fatty acid polyglycol esters, can be employed to control the development of foam. Suitable substances having a selective action, such as e.g. antibiotics, can be added to the medium to maintain the stability of plasmids. To maintain aerobic conditions, oxygen or oxygen-containing gas mixtures, such as e.g. air, are introduced into the culture. The temperature of the culture is usually 20° C. to 45° C., and preferably 25° C. to 40° C. Culturing is continued until a maximum of L-amino acid has formed. This target is usually reached within 10 hours to 160 hours.

The analysis of L-amino acids can be carried out by anion exchange chromatography with subsequent ninhydrin derivatization, as described by Spackman et al. (Analytical Chemistry, 30, (1958), 1190).

The following microorganism has been deposited at the Deutsche Sammlung für Mikrorganismen und Zellkulturen (DSMZ=German Collection of Microorganisms and Cell Cultures, Braunschweig, Germany) in accordance with the Budapest Treaty:

*Escherichia coli* JM109/pSUZ1 as DSM 13263.

SEQ ID NO 1 also contains the new devB gene. The process according to the invention is used for fermentative preparation of amino acids.

The abbreviations and designations used have the following meaning.

| | |
|---|---|
| lacZ: | segments of lacZα gene fragment |
| kan r: | kanamycin resistance |
| tal: | transaldolase gene |
| ori: | origin of replication of plasmid pBGS8 |
| BclI: | cleavage site of restriction enzyme BclI |
| EcoRI: | cleavage site of restriction enzyme EcoRI |
| HindIII: | cleavage site of restriction enzyme HindIII |
| PstI: | cleavage site of restriction enzyme PstI |
| SacI: | cleavage site of restriction enzyme SacI |

EXAMPLES

The following examples will further illustrate this invention. The molecular biology techniques, e.g. plasmid DNA isolation, restriction enzyme treatment, ligations, standard transformations of *Escherichia coli* etc. used are, (unless stated otherwise), described by Sambrook et al., (Molecular Cloning. A Laboratory Manual (1989) Cold Spring Harbour Laboratories, USA).

Example 1

Preparation of a Genomic Cosmid Gene Library from *Corynebacterium glutamicum* ATCC 13032

Chromosomal DNA from *Corynebacterium glutamicum* ATCC 13032 was isolated as described by Tauch et al. (1995, Plasmid 33:168-179) and partly cleaved with the restriction enzyme Sau3AI (Amersham Pharmacia, Freiburg, Germany, Product Description Sau3AI, Code no. 27-0913-02). The DNA fragments were dephosphorylated with shrimp alkaline phosphatase (Roche Molecular Biochemicals, Mannheim, Germany, Product Description SAP, Code no. 1758250). The DNA of the cosmid vector SuperCos1 (Wahl et al. (1987) Proceedings of the National Academy of Sciences USA 84:2160-2164), obtained from Stratagene (La Jolla, USA, Product Description SuperCos1 Cosmid Vector Kit, Code no. 251301) was cleaved with the restriction enzyme XbaI (Amersham Pharmacia, Freiburg, Germany, Product Description XbaI, Code no. 27-0948-02) and likewise dephosphorylated with shrimp alkaline phosphatase. The cosmid DNA was then cleaved with the restriction enzyme BamHI (Amersham Pharmacia, Freiburg, Germany, Product Description BamHI, Code no. 27-0868-04). The cosmid DNA treated in this manner was mixed with the treated ATCC13032 DNA and the batch was treated with T4 DNA ligase (Amersham Pharmacia, Freiburg, Germany, Product Description T4-DNA-Ligase, Code no. 27-0870-04). The ligation mixture was then packed in phages with the aid of Gigapack II XL Packing Extracts (Stratagene, La Jolla, USA, Product Description Gigapack II XL Packing Extract, Code no. 200217). For infection of the *E. coli* strain NM554 (Raleigh et al. 1988, Nucleic Acid Research 16:1563-1575) the cells were taken up in 10 mM $MgSO_4$ and mixed with an aliquot of the phage suspension. The infection and titering of the cosmid library were carried out as described by Sambrook et al. (1989, Molecular Cloning: A laboratory Manual, Cold Spring Harbor), the cells being plated out on LB agar (Lennox, 1955, Virology, 1:190) with 100 µg/ml ampicillin. After incubation overnight at 37° C., recombinant individual clones were selected.

Example 2

Isolation and Sequencing of the tal Gene

The cosmid DNA of an individual colony was isolated with the Qiaprep Spin Miniprep Kit (Product No. 27106, Qiagen, Hilden, Germany) in accordance with the manufacturer's instructions and partly cleaved with the restriction enzyme Sau3AI (Amersham Pharmacia, Freiburg, Germany, Product Description Sau3AI, Product No. 27-0913-02). The DNA fragments were dephosphorylated with shrimp alkaline phosphatase (Roche Molecular Biochemicals, Mannheim, Germany, Product Description SAP, Product No. 1758250). After separation by gel electrophoresis, the cosmid fragments in the size range of 1500 to 2000 bp were isolated with the QiaExII Gel Extraction Kit (Product No. 20021, Qiagen, Hilden, Germany). The DNA of the sequencing vector pZero-1, obtained from Invitrogen (Groningen, Holland, Product Description Zero Background Cloning Kit, Product No. K2500-01) was cleaved with the restriction enzyme BamHI (Amersham Pharmacia, Freiburg, Germany, Product Description BamHI, Product No. 27-0868-04). The ligation of the cosmid fragments in the sequencing vector pZero-1 was carried out as described by Sambrook et al. (1989, Molecular Cloning: A laboratory Manual, Cold Spring Harbor), the DNA mixture being incubated overnight with T4 ligase (Pharmacia Biotech, Freiburg, Germany). This ligation mixture was then electroporated (Tauch et al. 1994, FEMS Microbiol Letters, 123:343-7) into the *E. coli* strain DH5αMCR (Grant, 1990, Proceedings of the National Academy of Sciences U.S.A., 87:4645-4649) and plated out on LB agar (Lennox, 1955, Virology, 1:190) with 50 μg/ml zeocin. The plasmid preparation of the recombinant clones was carried out with Biorobot 9600 (Product No. 900200, Qiagen, Hilden, Germany). The sequencing was carried out by the dideoxy chain-stopping method of Sanger et al. (1977, Proceedings of the National Academy of Sciences U.S.A., 74:5463-5467) with modifications according to Zimmermann et al. (1990, Nucleic Acids Research, 18:1067). The "RR dRhodamin Terminator Cycle Sequencing Kit" from PE Applied Biosystems (Product No. 403044, Weiterstadt, Germany) was used. The separation by gel electrophoresis and analysis of the sequencing reaction were carried out in a "Rotiphoresis NF Acrylamide/Bisacrylamide" Gel (29:1) (Product No. A124.1, Roth, Karlsruhe, Germany) with the "ABI Prism 377" sequencer from PE Applied Biosystems (Weiterstadt, Germany).

The raw sequence data obtained were then processed using the Staden program package (1986, Nucleic Acids Research, 14:217-231) version 97-0. The individual sequences of the pZero1 derivatives were assembled to a continuous contig. The computer-assisted coding region analysis [sic] were prepared with the XNIP program (Staden, 1986, Nucleic Acids Research, 14:217-231). Further analyses were carried out with the "BLAST search program" (Altschul et al., 1997, Nucleic Acids Research, 25:3389-3402), against the non-redundant databank of the "National Center for Biotechnology Information" (NCBI, Bethesda, Md., USA). The nucleotide sequence obtained is shown in SEQ ID NO 1 and SEQ ID NO 3.

Example 3

Cloning of the tal Gene

PCR was used to amplify DNA fragments containing the entire tal gene of *C. glutamicum* 13032 and flanking upstream and downstream regions. PCR reactions were carried out using oligonucleotide primers designed from the sequence as determined in examples 1 and 2. Genomic DNA was isolated from *Corynebacterium glutamicum* ATTC13032 according to Heery and Dunican (Applied and Environmental Microbiology 59: 791-799 (1993)) and used as templates. The tal primers used were:

```
fwd. primer:
5' GGT ACA AAG GGT CTT AAG 3'   SEQ ID NO: 5 rev. primer:
5' GAT TTC ATG TCG CCG TTA 3'   SEQ ID NO: 6
```

PCR Parameters were as follows:
35 cycles
95° C. for 3 minutes
94° C. for 1 minute
47° C. for 1 minute
72° C. for 45 seconds
2.0 mM MgCl2
approximately 150-200 ng DNA template.

The PCR product obtained was cloned into the commercially available pGEM-T vector purchased from Promega Corp. (pGEM-T Easy Vector System 1, cat. no. A1360, Promega UK, Southampton, UK) using strain *E. coli* JM109 (Yanisch-Perron et al., Gene, 33: 103-119 (1985)) as a host. The entire tal gene was subsequently isolated from the pGEM T-vector on an Eco RI fragment and cloned into the lacZα EcoRI site of the *E. coli* vector pBGS8 (Spratt et al., Gene 41(2-3): 337-342 (1986)). The restriction enzymes used were obtained from Boehringer Mannheim UK Ltd. (Bell Lane, Lewes East Sussex BN7 1LG, UK) and used according to manufacturer's instructions. *E. coli* JMI09 was then transformed with this ligation mixture and electrotransformants were selected on Luria agar supplemented with isopropyl-thiogalactopyranoside (IPTG), 5-bromo-4-chloro-3-indolyl-galactopyranoside (XGAL) and kanamycin at concentrations of 1 mM, 0.02% and 50 mg/l respectively. Plates were incubated for twelve hours at 37° C. Plasmid DNA was isolated from one transformant, characterised by restriction enzyme analysis using Eco RI. This new construct was designated pSUZ 1.

---

The invention claimed is:

1. A process for the preparation of desired L-amino acids, which
    comprises carrying out the following steps:
    a) fermenting coryneform bacteria which produce the desired L-amino acids, in which a nucleotide sequence encoding a polypeptide with transaldolase activity having the amino acid sequence of SEQ ID NO:2 is overexpressed, by increasing the number of copies of the nucleotide sequence in the coryneform bacteria relative to the number of copies that is normally present in a wild-type bacteria of the same strain; and
    b) concentrating the desired L-amino acids in the medium or in the cells of the bacteria.

2. The process of claim 1, wherein L-lysine is a desired L-amino acid that is produced by the coryneform bacteria, and additionally wherein one or more genes from *C. glutamicum* chosen from the group consisting of
    a dapA gene which encodes dihydrodipicolinate synthase,
    a lysC gene which encodes a feedback resistant aspartate kinase,
    a gap gene which encodes glycerolaldehyde 3-phosphate dehydrogenase,
    a pyc gene which encodes pyruvate carboxylase,
    a mqo gene which encodes malate-quinone oxidoreductase,
    a tkt gene which encodes transketolase,
    a gnd gene which encodes 6-phosphogluconate dehydrogenase,
    a zwf gene which encodes glucose 6-phosphate dehydrogenase,
    a lysE gene which encodes LysE polypeptide,
    a zwa1 gene which encodes Zwa1 polypeptide,
    a eno gene which encodes enolase, and
    a opcA gene which encodes OpcA polypeptide
    is overexpressed in the coryneform bacteria, wherein said overexpression is achieved by using an overexpression plasmid vector.

3. The process of claim 1, wherein L-threonine is a desired L-amino acid that is produced by the coryneform bacteria, and additionally wherein one or more genes from *C. glutamicum* chosen from the group consisting of
    a gap gene which encodes glyceraldehyde 3-phosphate dehydrogenase,
    a pyc gene which encodes pyruvate carboxylase,
    a mqo gene which encodes malate:quinone oxidoreductase,
    a tkt gene which encodes transketolase,
    a gnd gene which encodes 6-phosphogluconate dehydrogenase,
    a zwf gene which encodes glucose 6-phosphate dehydrogenase,
    a thrE gene which encodes ThrE polypeptide,
    a zwa1 gene which encodes Zwa1 polypeptide,
    a eno gene which encodes enolase, and
    a opcA gene which encodes OpcA polypeptide
    is overexpressed, in the coryneform bacteria, wherein said overexpression is achieved by using an overexpression plasmid vector.

4. The process of claim 1, wherein said nucleotide sequence comprises the nucleotide sequence of nucleotides 2471 to 3550 of SEQ ID NO: 1.

5. The process of claim 1, wherein the number of copies of the nucleotide sequence of nucleotides 2471 to 3550 of SEQ ID NO: 1 in the coryneform bacteria is increased relative to the number of copies that is normally present in wild-type bacteria of the same species.

6. The process of claim 1, wherein said nucleotide sequence is present in a plasmid in the coryneform bacteria.

7. The process of claim 1, wherein said nucleotide sequence is integrated into the chromosome of the coryneform bacteria.

8. The process of claim 1, wherein one or more nucleotide sequences encoding one or more enzymes of a biosynthetic pathway of the desired L-amino acids in addition to said polypeptide with transaldolase activity is overexpressed in the coryneform bacteria, wherein said overexpression is achieved by using an overexpression plasmid vector.

9. The process of claim 1, additionally wherein one or more genes chosen from the group consisting of
    a pck gene which encodes phosphoenol pyruvate carboxykinase,
    a pgi gene which encodes glucose 6-phosphate isomerase,
    a poxB gene which encodes pyruvate oxidase, and
    a zwa2 gene which encodes Zwa2 polypeptide
    is or are eliminated in the coryneform bacteria.

10. The process of claim 9, wherein the coryneform bacteria produce one or more desired L-amino acids selected from the group consisting of L-lysine, L-threonine, L-isoleucine and L-tryptophan.

11. The process of claim 1, wherein the coryneform bacteria produces one or more desired L-amino acids selected from the group consisting of L-lysine, L-threonine, L-isoleucine and L-tryptophan.

12. The process of claim 1, wherein the coryneform bacteria are of the genus *Corynebacterium*.

13. The process of claim 12, wherein the coryneform bacteria are of the species *Corynebacterium glutamicum*.

14. The process of claim 1, which further comprises the step: c) isolating the desired L-amino acids.

15. A process for the preparation of an L-amino acid, comprising:
    a) altering a coryneform bacteria capable of producing the L-amino acid, wherein the altering comprises increasing expression of the polypeptide of SEQ ID NO:2 and has the catalytic activity of transaldolase, further wherein the increasing expression of the polypeptide of SEQ ID NO:2 is achieved by increasing the number of copies of a nucleotide sequence encoding the polypeptide of SEQ ID NO:2 in the coryneform bacteria relative to the number of copies normally present in a wild-type bacteria of the same strain;
    b) fermenting a culture medium with the coryneform bacteria, producing the L-amino acid thereby; and
    c) isolating the L-amino acid.

16. A process for the preparation of an L-amino acid, comprising:
    a) altering a coryneform bacteria capable of producing the L-amino acid, wherein the altering comprises increasing expression of the polypeptide of SEQ ID NO:2 and has the catalytic activity of transaldolase, further wherein the increasing expression of the polypeptide of SEQ ID NO:2 is achieved by using an overexpression plasmid vector comprising a promoter operably linked to a nucleotide sequence encoding the polypeptide of SEQ ID NO:2;
    b) fermenting a culture medium with the coryneform bacteria, producing the L-amino acid thereby; and
    c) isolating the L-amino acid.

* * * * *